(12) United States Patent
Tabor et al.

(10) Patent No.: US 10,413,442 B2
(45) Date of Patent: Sep. 17, 2019

(54) SUPPORT CUSHION HAVING A DISPOSABLE ABSORBENT LAYER

(71) Applicant: BANYAN LICENSING L.L.C., Charlotte, NC (US)

(72) Inventors: Calvin Gerrit Tabor, Charlotte, NC (US); E. Scott Davis, Lake Wylie, SC (US)

(73) Assignee: Banyan Licensing L.L.C., Charlotte, NC (US)

(*) Notice: Subject to any disclaimer, the term of this patent is extended or adjusted under 35 U.S.C. 154(b) by 375 days.

(21) Appl. No.: 15/110,184

(22) PCT Filed: Jan. 9, 2015

(86) PCT No.: PCT/IB2015/000679
§ 371 (c)(1),
(2) Date: Jul. 7, 2016

(87) PCT Pub. No.: WO2015/110926
PCT Pub. Date: Jul. 30, 2015

(65) Prior Publication Data
US 2016/0324328 A1    Nov. 10, 2016

Related U.S. Application Data

(60) Provisional application No. 61/926,113, filed on Jan. 10, 2014.

(51) Int. Cl.
*A61F 5/48* (2006.01)
*A61G 5/10* (2006.01)
(Continued)

(52) U.S. Cl.
CPC ............ *A61F 5/485* (2013.01); *A01K 1/0157* (2013.01); *A01K 1/0353* (2013.01); *A47C 21/06* (2013.01);
(Continued)

(58) Field of Classification Search
CPC .... A47G 9/00; A47G 9/10; A47G 2009/1018; A47C 27/007; A47C 27/22;
(Continued)

(56) References Cited

U.S. PATENT DOCUMENTS 3,691,570 A * 9/1972 Gaines .................. A47C 27/12
428/907
3,965,508 A * 6/1976 Hunter ................ A47C 27/085
297/452.41

(Continued)

FOREIGN PATENT DOCUMENTS

| GB | 2042343 A | 1/1979 | |
|---|---|---|---|
| WO | 2008155126 A1 | 12/2008 | |
| WO | WO-2008155126 A1 * | 12/2008 | ............... A61F 5/48 |

OTHER PUBLICATIONS

International Search Report for International Patent Application No. PCT/IB2015/000679 dated Mar. 20, 2015.
(Continued)

*Primary Examiner* — Robert G Santos
*Assistant Examiner* — David R Hare
(74) *Attorney, Agent, or Firm* — Moore & Van Allen PLLC; Henry B. Ward

(57) ABSTRACT

A liquid absorbent support cushion for a user is disclosed comprising a first member having first and second surfaces, the first member constructed of a first material in which the first member is substantially liquid permeable and the first material is substantially liquid impervious. The cushion includes a second member having first and second surfaces, the second member constructed of a second material in which the second member is substantially liquid permeable and the second material is substantially liquid impervious. The cushion also includes a third member, the third member is liquid absorbent; and wherein the second member is positioned between the first and third members and wherein
(Continued)

the first, second and third members are constructed such that liquid passing through the first and second members is absorbed by the third member.

12 Claims, 3 Drawing Sheets

(51) Int. Cl.
    *A61F 13/47*     (2006.01)
    *A01K 1/015*     (2006.01)
    *A01K 1/035*     (2006.01)
    *A47C 21/06*     (2006.01)
    *A47C 27/22*     (2006.01)
    *A47G 9/00*     (2006.01)
    *A61F 13/15*     (2006.01)

(52) U.S. Cl.
    CPC ............... *A47C 27/22* (2013.01); *A47G 9/00* (2013.01); *A61F 13/47* (2013.01); *A61G 5/1043* (2013.01); *A61F 2013/15154* (2013.01); *A61F 2013/15186* (2013.01)

(58) Field of Classification Search
    CPC .. A01K 1/0353; A01K 1/0157; A61G 5/1043; A61G 5/1045; A61F 13/47; A61F 5/485; A61F 2013/15186; A61F 2013/15154
    See application file for complete search history.

(56) References Cited

U.S. PATENT DOCUMENTS

| | | | | |
|---|---|---|---|---|
| 4,045,833 A * | 9/1977 | Mesek | ............... | A61F 5/485 248/205.3 |
| 4,069,366 A * | 1/1978 | Hoey | ............... | A61L 15/425 442/30 |
| 4,173,046 A * | 11/1979 | Gallagher | ............... | A61F 5/485 5/484 |
| 4,813,944 A * | 3/1989 | Haney | ............... | A61F 13/5323 5/484 |
| 4,961,982 A * | 10/1990 | Taylor | ............... | A61F 5/485 112/475.08 |
| 4,965,900 A * | 10/1990 | Smith | ............... | A47C 21/046 5/484 |
| 5,099,532 A * | 3/1992 | Thomas | ............... | A61F 5/485 5/484 |
| 5,444,900 A * | 8/1995 | Shawhan | ............... | A61F 5/485 27/1 |
| 5,685,257 A * | 11/1997 | Feibus | ............... | A01K 1/0353 119/28.5 |
| 5,715,772 A * | 2/1998 | Kamrath | ............... | A01K 1/0157 119/169 |
| 6,412,801 B1 * | 7/2002 | Izuchukwu | ............... | A61G 5/1043 128/204.18 |
| 7,361,803 B2 * | 4/2008 | Miskie | ............... | A61F 13/505 604/378 |
| 8,914,923 B2 * | 12/2014 | Smith | ............... | A47C 31/105 5/484 |
| 2001/0042518 A1 * | 11/2001 | Ikegami | ............... | A01K 1/0107 119/161 |
| 2004/0093671 A1 * | 5/2004 | Bjomberg | ............... | A61F 5/485 5/484 |
| 2011/0208145 A1 * | 8/2011 | Zhang | ............... | A61F 5/485 604/368 |
| 2012/0297545 A1 * | 11/2012 | Essers | ............... | A47C 27/005 5/691 |
| 2013/0198955 A1 | 8/2013 | Lishnevsky et al. | | |

OTHER PUBLICATIONS

Written Opinion for International Patent Application No. PCT/IB2015/000679 dated Mar. 20, 2015.

* cited by examiner

SUPPORT CUSHION HAVING A DISPOSABLE ABSORBENT LAYER

CROSS-REFERENCES TO RELATED APPLICATIONS

This applications claims priority under 35 U.S.C. § 119 of U.S. Provisional Patent Application No. 61/926,113, entitled SUPPORT CUSHION HAVING A DISPOSABLE ABSORBENT LAYER, filed on Jan. 10, 2014, the entire contents of which is incorporated herein by reference.

BACKGROUND OF THE INVENTION

Field of the Invention

The present invention relates generally to body support cushion having a disposable absorbent layer.

Description of Related Art

There are a number of conventional support cushions designed to be used by individuals suffering urinary incontinence or otherwise in circumstances involving liquid or moisture, such as pet beds or cushions. As used herein, "support cushion" may include a cushion to support a user in the seated position or an elongate cushion to support a user when lying in a substantially horizontal or semi-horizontal position. As used herein, a "user" may include an adult, a child, an infant or a pet.

Some of these conventional support cushions include a liquid a impermeable material or barrier, such as vinyl, or polymer coated fabric, on the outside of the support cushion to prevent liquid for penetrating the support cushion. While such barriers keep the interior of the support cushion dry, such barriers may also result in the concentration of moisture or liquid under the user where the user's weight creates a concave depression in the cushion that retains liquid. This can lead to irritation to the user's skin in the area of moisture concentration.

Other conventional support cushion structures include an absorbent layer comprising a liquid permeable cover surface, an absorbent layer, and a support cushion. The absorbent layer is placed in such a way that liquid absorption occurs on the top layer of the support cushion structure. In such cases, if the amount of liquid increases beyond the capacity of the absorption layer, there is substantial risk of liquid seepage into the support cushion. As most support cushions are designed to be liquid permeable, the cleaning process involved can be difficult and tedious. In addition, as the absorbent top layer typically conforms to the user's body, if the amount of liquid increases beyond the capacity of the absorption layer, the distance of separation between the user and the liquid reduces materially. Accordingly, there remains a need for a support cushion having a disposable absorbent layer with substantial separation between the user and the liquid absorbed.

SUMMARY OF THE INVENTION

The present invention comprises a liquid absorbent support cushion for a user. The cushion comprises a first member having first and second surfaces, the first member constructed of a first material in which the first member is substantially liquid permeable and the first material is substantially liquid impervious. In one embodiment, the first member is constructed of a spacer fabric.

The cushion comprises a second member having first and second surfaces, the second member constructed of a second material in which the second member is substantially liquid permeable and the second material is substantially liquid impervious. In one embodiment, the second member is constructed of a thermoplastic.

The cushion comprises a third member that is liquid absorbent. The second member is positioned between the first and third members and wherein the first, second and third members are constructed such that liquid passing through the first and second members is absorbed by the third member. In one embodiment, the third member comprises a superabsorbent polymer.

In one embodiment, at least one of the first and second members is air permeable. In another embodiment, at least one of the first and second members comprises a super-hydrophobic coating.

In yet another embodiment, the cushion comprises a fourth member that is liquid impervious and that at least partially encloses the third and second members. In one embodiment, at least a portion of the fourth member is detachably secured to the first member.

The present invention also comprises a method of maintaining a support cushion. The method comprises providing a support cushion comprising first member having first and second surfaces, the first member constructed of a first material in which the first member is substantially liquid permeable and the first material is substantially liquid impervious. In one embodiment, the first member is constructed of a spacer fabric. The support cushion further comprises a second member having first and second surfaces, the second member constructed of a second material in which the second member is substantially liquid permeable and the second material is substantially liquid impervious. In one embodiment, the second member is constructed of a thermoplastic. In another embodiment, at least one of the first and second members is air permeable. In yet another embodiment, at least one of the first and second members comprises a super-hydrophobic coating. The support cushion further comprises a third member, the third member is liquid absorbent and wherein the second member is positioned between the first and third members and wherein the first, second and third members are constructed such that liquid passing through the first and second members is absorbed by the third member. In one embodiment, the third member comprises a superabsorbent polymer. The method further comprising removing the third member and inserting a new third member.

In one embodiment, the support cushion further comprises a fourth member that is liquid impervious and that at least partially encloses the third and second members. In another embodiment, at least a portion of the fourth member is detachably secured to the first member and wherein the removing step comprising detaching the fourth member from the first member.

BRIEF DESCRIPTION OF THE DRAWINGS

The foregoing and other advantages and features of the invention, and the manner in which the same are accomplished, will become more readily apparent upon consideration of the following detail description of the invention taken in conjunction with the accompanying drawings, which illustrate preferred and exemplary embodiments and which are not necessarily drawn to scale, wherein.

DETAILED DESCRIPTION OF AN EMBODIMENT OF THE INVENTION

The present invention now will be described more fully hereinafter with reference to the accompanying drawings, in which some, but not all embodiments of the invention are shown. This invention may be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
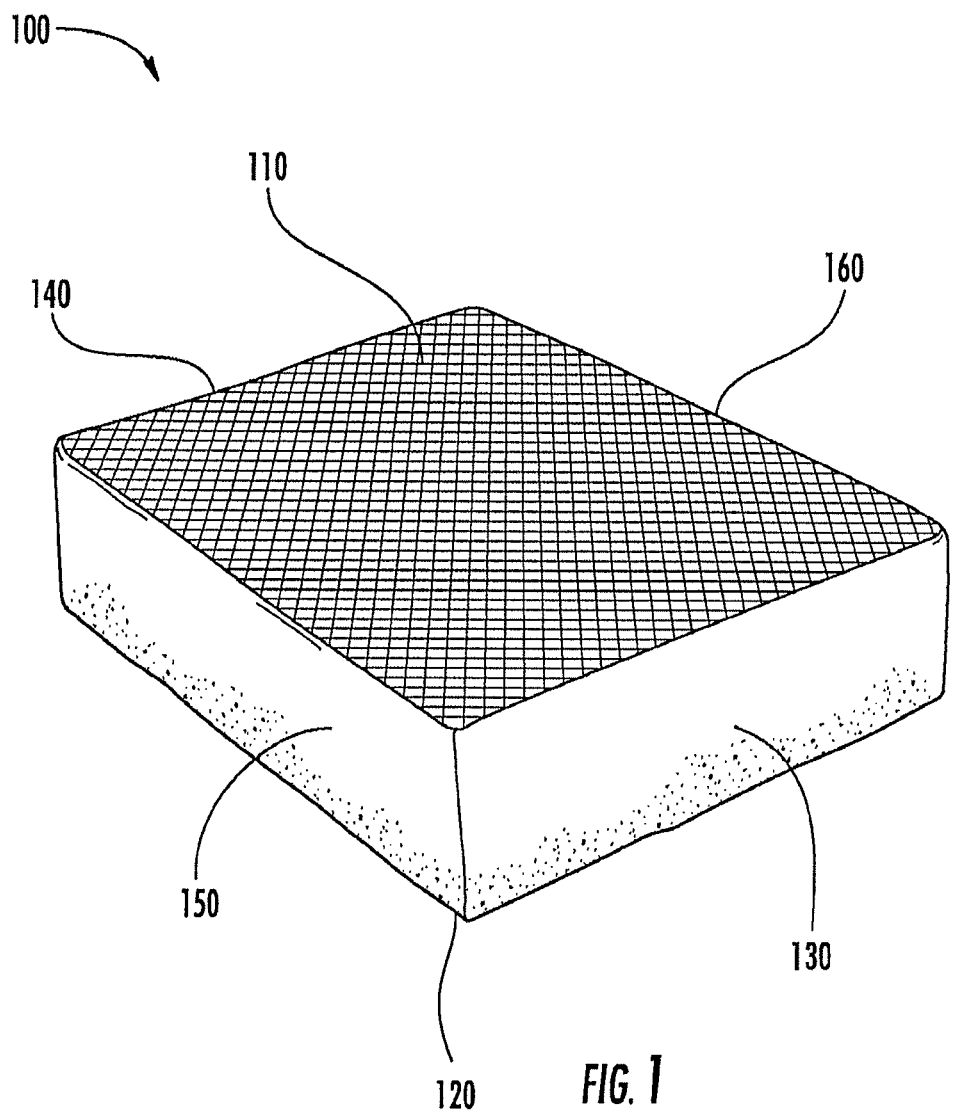
FIG. 1 is a perspective view of a body support having a disposable absorbent layer.
Figure 2:
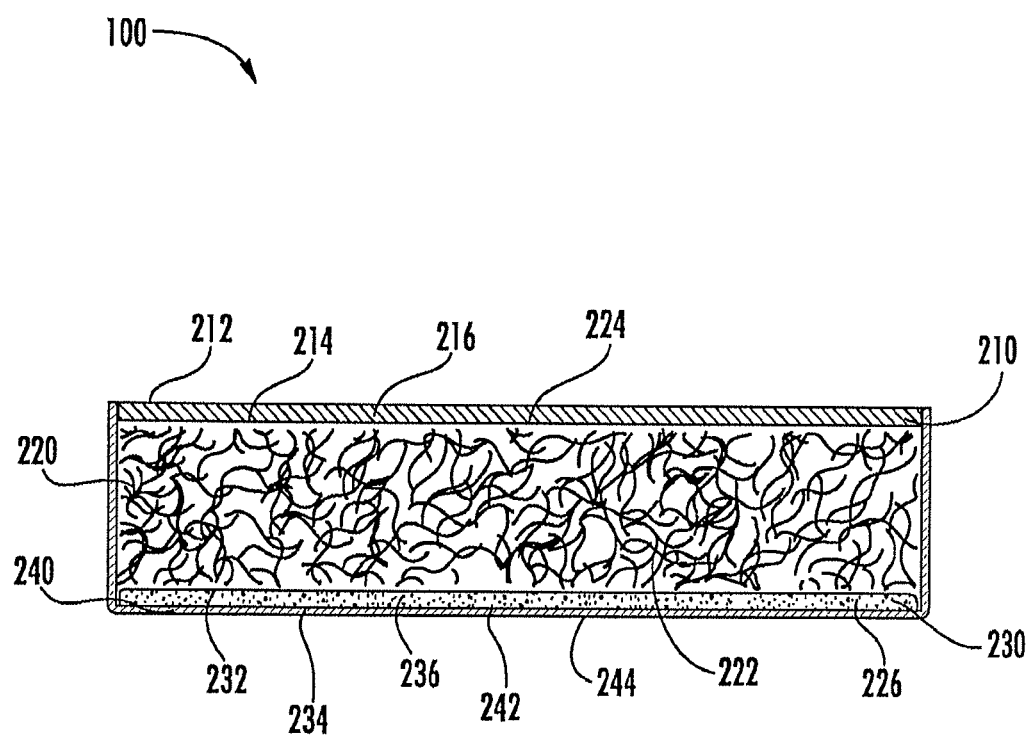
FIG. 2 is a cross-sectional view of the support cushion of FIG. 1.
Figure 3:
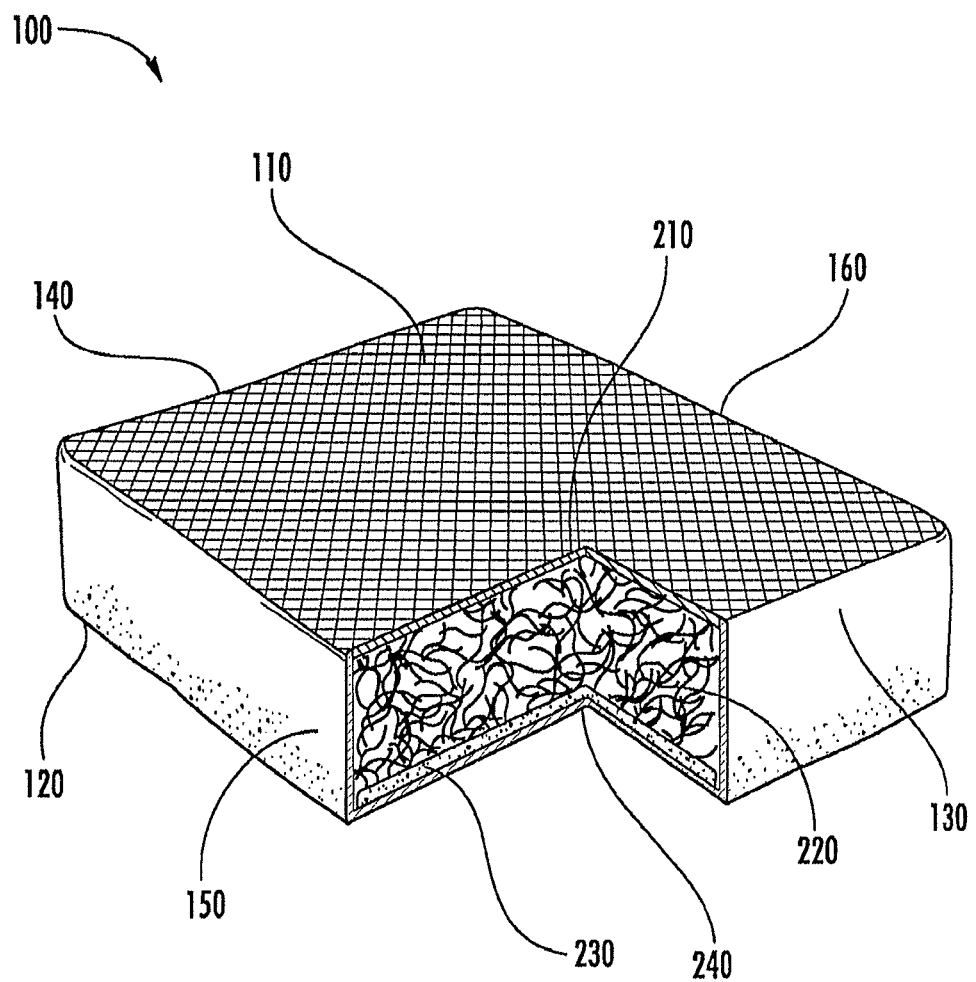
FIG. 3 is a cut-away view of the support cushion of FIG. 1.

FIGS. 1 through 3 illustrate a support cushion 100, according to one embodiment of the present invention. Referring to FIG. 1, the support cushion 100 may have a rectangular shape, although its overall shape can be made to vary widely. The support cushion 100 typically has six surfaces, defined for the purposes of this document as a top (or user facing) surface 110, a bottom surface 120, a front surface 130, a back surface 140, a left-lateral surface 150 and a right-lateral surface 160. Further, the support cushion 100 has a width defined as a distance from the left-lateral surface 150 to the right-lateral surface 160, a depth defined as a distance from the front surface 130 to the back surface 140, and a thickness defined as a distance from the top surface 110 to the bottom surface 120. These dimensions may be varied to suit a particular need. Because the actual shape of the support cushion 100 may not be exactly or even approximately rectangular, the width, depth and thickness distances are to be measured from the extreme points on every defined surface. The invention is not limited to any particular shape for the support cushion 100.

Referring to FIG. 2, the support cushion 100 comprises a first member 210, a second member 220, a third member 230, and a fourth member 240 wherein each member defines a first and second surface.

The first member 210 of the support cushion 100 may be constructed using a variety of materials, including synthetic and natural fabrics and natural/synthetic blends, provided that the first member 210 itself is substantially air and liquid permeable, but that the material(s) used to form the first member 210 is substantially liquid impermeable. In other words, the material that is used to form the first member 210 should be substantially non-absorbent and/or substantially impervious to liquid such that liquids will flow through the first member 210 with minimal resistance and, further, that the first member 210 will retain, at most, a minimal amount of such liquid so that any such liquid is quickly and efficiently transported away from the top surface 110 and, thus, the user. For purpose of example, and not limitation, the first member 210 may be constructed of polyester or silk or cotton fibers having a thermoplastic or other liquid impervious coating. In one embodiment, the first member 210 is at least partially constructed of a spacer fabric, also commonly referred to as 3-D mesh. Spacer fabrics have a sandwich construction and feature a first layer 212, a second layer 214, and a third layer 216 in between the first 212 and second 214 layers. The third/inner layer 216 may take a variety of shapes and configurations including tubes, pleats, or other engineered forms. The three-layered construction forms openings that enable air and liquid to flow through the first layer 212, to thereby ventilate the support cushion 100 with cool air and to allow liquid to pass through to the second member 220. In one embodiment, the spacer fabric is approximately 2 to 3 millimeter in thickness and provides a level of comfort between the second member 220 and the user. Typically, the configuration of the first member 210 will be substantially the same as the seat cushion 100. As illustrated in FIGS. 1-3, the first member 210 has a rectangular shape defining a top surface, a bottom surface, a front surface, a back surface, a left-lateral surface and a right-lateral surface defining a length, width, and depth.

The second member 220 of the support cushion 100 is constructed as a cushion for seating support and/or as a mattress. In some embodiments, the second member 220 may have consistent firmness throughout. In other embodiments, the firmness of the second member 220 may vary based on the location of anticipated load, i.e., the second member may be more firm where the anticipated load is higher and less firm where the anticipated load is lower, to optimize support and pressure distribution. In some embodiments, the second member 220 is preferably compressible and resilient. The second member 220 itself should be substantially air and liquid permeable, but that the material(s) used to form the second member 220 should be substantially liquid impermeable. In other words, like the first member 210, the material that is used to form the second member 210 should be substantially non-absorbent and/or substantially impervious to liquid such that liquids will flow through the second member 220 with minimal resistance and, further, that the second member 220 will retain, at most, a minimal amount of such liquid. In one embodiment, the second member 220 is constructed using flexible thermoplastic material such as polyethylene, or any other thermoplastic resins such as polypropylene, polystyrene, or various foams or mesh materials or the like that can be formed into a relatively supportive structure for use as cushion. Typically, polyethylene is prepared by polymerizing ethylene at high pressure and high temperature in the presence of trace oxygen. Polyethylene can be molded into different shapes and is used in many applications for its moisture resistant characteristics. In one embodiment, the polyethylene fibers are arranged to form the second member 220 into a cushion 222 comprising internal cavities to facilitate air and liquid flow through the second member 220. This allows adequate air circulation within the body of the cushion 222 by dissipating heat and humidity into the ambient atmosphere, as well as allowing liquid passing through the first member 210 to also pass through the second member 220 to the third member 230 to further the distance of such liquid from the user and, thus, resulting in more comfortable and prolonged use. While the polyethylene fibers are substantially liquid impervious, the second member 220 is substantially liquid permeable retaining substantially no liquid. Typically, the configuration of the second member 220 will be substantially the same as the seat cushion 100. As illustrated in FIGS. 1-3, the second member 220 has a rectangular shape defining a top surface, a bottom surface, a front surface, a back surface, a left-lateral surface and a right-lateral surface defining a length, width, and depth. The second member 220 may be constructed in such a way that prolonged use of the support cushion 100 creates deformation patterns that are restricted to the top surface 110 and do not affect the bottom surface 120 due to the distribution of the downward forces created by the user over a broader area. Further, the top surface 110 may be constructed to be flat or may be constructed to be contoured to conform to the user's body and the bottom surface 120 may be constructed to be flat or may be constructed to be contoured to conform to the seating surface, if such surface is contoured. In one embodiment, the second member 220 may include one layer and in other embodiments the second member may comprise two or more layers that are unattached or attached together by gluing, ultrasonically welding, heat sealing or using mechanical fasteners provided that the method of attachment does not material restrict the passage of liquid through the second member 220 or materially increase the amount of liquid retained by the second member.

The air and liquid permeability of the first member 210 and second member 220 is advantageous for several reasons. First, the air and liquid permeability facilitates the process of washing/cleaning, rinsing and drying the first member 210 and second member 220 as the water or other cleaning agents pass through the first member 210 and second member 220 to wash and clean the first member 210 and second member 220. Thereafter, air passing through the first member 210 and second member 220 quickly dries the first member 210 and second member 220. Second, the air and liquid permeability facilitates transporting liquid away from the top surface 110 and, thus, the user. This makes the present invention useful in applications such as a cushion for wheel chairs and mattresses for use in hospital, hospices and similar applications.

In one embodiment, the first member 210 and the second member 220 may be lined with a super-hydrophobic coating composition that can be used to make the surfaces liquid impervious and/or to increase how quickly liquid moves through the first member 210 and second member 220. Super-hydrophobic coatings also are advantageous as such coatings have a "self-cleaning" property such that dirt, bacteria, spores, or other substances that come in contact with the surface cannot readily adhere to the coating and can be washed off by water. Typically, the super-hydrophobic coating can be applied by a single and easy spraying method and the super-hydrophobic property can be achieved by drying the film at room temperature for 5 to 10 minutes.

The third member 230 of the support cushion 100 is a disposable liquid absorbent member. In one embodiment, the third member 230 comprises a liquid permeable first layer 232, a liquid impermeable second layer 234, and an absorbent core 236 interposed between the first layer 232 and the second layer 234 and absorbs the liquid permeated through the first layer 232. In other embodiments, the third member 230 can comprise an absorbent core encapsulated inside a liquid impermeable cover. Typically, the absorbent core 236 is constructed using a superabsorbent polymer (SAP) capable of absorbing and retaining extremely large amounts of liquid relative to their own mass. In one embodiment, the third member 230 may include a relatively bulky cushion layer constituted by hydrophilic fibers provided between the first layer 232 and the absorbent core 236. The absorbent third member 230 is positioned within the support cushion 100 such liquid passing through the first member 210 and the second member 220 comes into contact with the third member 230 and is absorbed by the absorbent core 236. Advantageously, the third member 230 can be periodically disposed of and replaced by accessing an opening in the support cushion 100, as discussed below. Typically, the configuration of the third member 230 will be substantially the same as the seat cushion 100. As illustrated in FIGS. 1-3, the second member 230 has a rectangular shape defining a top surface, a bottom surface, a front surface, a back surface, a left-lateral surface and a right-lateral surface defining a length, width, and depth.

The fourth member 240 of the support cushion 100 is preferably formed from a liquid impermeable material such as vinyl or polymer coated fabric that covers the bottom surface of the third member 230 and extends from the bottom surface of the third member along the front surfaces, back surfaces, left-lateral surfaces and right-lateral surfaces of the third member, second member 220, and first member 210. The fourth member 240 may be constructed using any number of pieces of material that are formed integrally or attached together, such as by sewing, gluing, ultrasonically welding, heat sealing, etc. Preferably, the fourth member 240 is at least partially attached to the front surface, back surface, left-lateral surface and right-lateral surface of the first member 210 and that at least a portion of such attachment is configured to be detached (e.g., zippered, buttoned, snapped, hook and loop fastened, etc.) so that the interior of the cushion can be accessed to allow the third member 230 to be disposed of and replaced. The fourth member 240 advantageously retains any liquid that passes through the first member 210 and the second member 220 until such liquid can be absorbed by the third member 230 to thereby prevent the liquid from spilling or seeping from the support cushion 100 on to the adjacent surfaces. In one embodiment, the fourth member 240 may include flanges or other protuberances along the front surface, back surface, left-lateral surface and right-lateral surface for retaining the third member. In one aspect, the fourth member 240 is constructed to at least partially enclose the bottom surface 120, the left-lateral surface 150, the right-lateral surface 160, the back surface 140 and the front surface 130. For example, the fourth member 240 may be formed from five pieces of material, each of which substantially forms one of the bottom surface 120, front surface 130, back surface 140, left lateral surface 150, and right-lateral surface 160 of the support cushion 100. Alternatively, any single piece may be formed and its edges attached to itself so that the fourth member 240 consists of that single piece. It is to be understood that some pieces of the fourth member 240 may overlap other pieces.

In an embodiment of the present invention, the first member 210, the second member 220, third member 230, and the fourth member 240 are organized such that there is substantial separation between the liquid absorbed in the third member 230 and the user in contact with the first member 210. In one embodiment, the four members are positioned in such a way that the first layer 212 of the first member 210 defines the top of the support cushion 100 and is in contact with the user; the second layer 214 of the first member 210 is in contact with the top surface 224 of the second member 220; the bottom surface 226 of the second member 220 is in contact with the first layer 232 of the third member 230; and the second layer 234 of the third member 230 is in contact with the top surface 242 of the fourth member 240; and the bottom surface 244 of the fourth member 240 defines the base of the support cushion 100.

Optionally, the support cushion 100 may include a cover (not shown) at least partially enclosing the support cushion 100. In one embodiment, the cover may at least partially enclose the first member 210, the second member 220, the third member 230, and the fourth member 240. For covers made of multiple pieces, the pieces may be attached using any one of a variety of known methods, including, without limitation, sewing, gluing, ultrasonically welding, heat sealing, zippering, hook-and-loop fastening, buttons, snaps, buckles or the like. For example, the cover may be formed from six pieces of material, each of which substantially forms one of the six surfaces of the support cushion 100.

Alternatively, any single piece may form part of or all of the one or more surfaces of the support cushion 100. Also, it follows that a single piece may be formed and its edges attached to itself so that the cover consists of that that single piece and any attachment mechanisms or methods. It is to be understood that some pieces of the cover may overlap other pieces. The cover normally includes an opening to allow access to the internal components of the support cushion 100 within it. The opening typically includes a zipper that runs along the back surface 140 and parts of the left 150 and right 160 surfaces of the cushion 100. When the zipper is opened, the cover is positioned to accept the internal components. When the zipper is closed, the internal components are, in one embodiment, completely enclosed within the cover. Alternatively, the opening can take many different forms, including a surface that has one or more of its edges attached to the other surfaces by hook-and-loop fasteners, snaps, buttons, buckles, or any other fastening or enclosing mechanism.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. A liquid absorbent support cushion for a user, comprising:
    a first member having first and second surfaces, the first member constructed of a first material in which the first member is substantially liquid permeable and the first material is substantially liquid impervious;
    a second member having first and second surfaces, the second member constructed of a second material in which the second member is substantially liquid permeable and the second material is substantially liquid impervious;
    a third member having first and second surfaces, the third member is liquid absorbent; and
    a fourth member that is liquid impervious, the fourth member at least partially enclosing the third and second members, being positioned adjacent to the second surface of the third member and being detachably secured to the first member,
    wherein the second member is positioned between the first and third members such that the second surface of the second member is adjacent the first surface of the third member, and wherein the first, second and third members are constructed such that liquid passing through the first and second members is absorbed by the third member.

2. A support cushion according to claim 1, wherein the first member is constructed of a spacer fabric.

3. A support cushion according to claim 1, wherein the second member is constructed of a thermoplastic.

4. A support cushion according to claim 1, wherein the third member comprises a superabsorbent polymer.

5. A support cushion according to claim 1, wherein at least one of the first and second members is air permeable.

6. A support cushion according to claim 1, wherein at least one of the first and second members is coated with a liquid impervious coating comprising a super-hydrophobic coating.

7. A method of maintaining a support cushion, comprising:
    providing a support cushion comprising:
        a first member having first and second surfaces, the first member constructed of a first material in which the first member is substantially liquid permeable and the first material is substantially liquid impervious;
        a second member having first and second surfaces, the second member constructed of a second material in which the second member is substantially liquid permeable and the second material is substantially liquid impervious;
        a third member having first and second surfaces, the third member is liquid absorbent; and
        a fourth member that is liquid impervious, the fourth member at least partially enclosing the third and second members, being positioned adjacent to the second surface of the third member and being detachably secured to the first member,
    wherein the second member is positioned between the first and third members, such that the second surface of the second member is adjacent the first surface of the third member, and wherein the first, second and third members are constructed such that liquid passing through the first and second members is absorbed by the third member;
    in response to detaching the fourth member from the first member, removing the third member, and inserting a new third member; and
    re-attaching the fourth member to the first member.

8. A method according to claim 7, wherein the first member is constructed of a spacer fabric.

9. A method according to claim 7, wherein the second member is constructed of a thermoplastic.

10. A method according to claim 7, wherein the third member comprises a superabsorbent polymer.

11. A method according to claim 7, wherein at least one of the first and second members is air permeable.

12. A method according to claim 7, wherein at least one of the first and second members is coated with a liquid impervious coating comprises a super-hydrophobic coating.

* * * * *